(12) United States Patent
Threlkeld et al.

(10) Patent No.: US 7,939,686 B2
(45) Date of Patent: May 10, 2011

(54) METHOD FOR PROVIDING ANTIMICROBIAL COMPOSITE YARNS, COMPOSITE FABRICS AND ARTICLES MADE THEREFROM

(75) Inventors: James Threlkeld, Indian Trail, NC (US); Nathaniel H. Kolmes, Hickory, NC (US)

(73) Assignee: Supreme Corporation, Conover, NC (US)

( * ) Notice: Subject to any disclaimer, the term of this patent is extended or adjusted under 35 U.S.C. 154(b) by 251 days.

(21) Appl. No.: 10/785,060

(22) Filed: Feb. 25, 2004

(65) Prior Publication Data

US 2005/0186259 A1    Aug. 25, 2005

(51) Int. Cl.
*C07F 7/08* (2006.01)
(52) U.S. Cl. .................... 556/425; 106/287.11
(58) Field of Classification Search ............ 424/400
See application file for complete search history.

(56) References Cited

U.S. PATENT DOCUMENTS

| | | | |
|---|---|---|---|
| 3,899,616 A | 8/1975 | Simonelli | |
| 4,777,789 A | 10/1988 | Kolmes et al. | |
| 4,838,017 A | 6/1989 | Kolmes et al. | |
| 4,936,085 A | 6/1990 | Kolmes et al. | |
| 4,993,651 A * | 2/1991 | Ohno et al. | 242/570 |
| 5,119,512 A | 6/1992 | Dunbar et al. | |
| 5,177,948 A | 1/1993 | Kolmes et al. | |
| 5,382,264 A | 1/1995 | Sharma | |
| 5,423,168 A | 6/1995 | Kolmes et al. | |
| 5,500,025 A | 3/1996 | Sharma | |
| 5,565,265 A * | 10/1996 | Rubin et al. | 442/92 |
| 5,567,372 A | 10/1996 | Nohr et al. | |
| 5,628,172 A | 5/1997 | Kolmes et al. | |
| 5,632,137 A | 5/1997 | Kolmes et al. | |
| 5,644,907 A | 7/1997 | Kolmes et al. | |
| 5,655,358 A | 8/1997 | Kolmes | |
| 5,707,736 A * | 1/1998 | Levy et al. | 428/375 |
| 5,845,476 A | 12/1998 | Kolmes | |
| 6,160,196 A * | 12/2000 | Knieler et al. | 602/48 |
| 6,212,914 B1 | 4/2001 | Kolmes et al. | |
| 6,230,524 B1 | 5/2001 | Kolmes et al. | |
| 6,341,483 B1 | 1/2002 | Kolmes et al. | |
| 6,349,531 B1 | 2/2002 | Kolmes et al. | |
| 6,351,932 B1 | 3/2002 | Hummel | |
| 6,363,703 B1 | 4/2002 | Kolmes et al. | |
| 6,367,290 B2 | 4/2002 | Kolmes et al. | |
| 6,381,940 B1 | 5/2002 | Kolmes et al. | |
| 6,384,254 B1 * | 5/2002 | Omura | 556/425 |
| 6,467,251 B1 | 10/2002 | Kolmes | |
| RE38,136 E | 6/2003 | Kolmes | |
| 6,596,657 B1 | 7/2003 | Shalaby | |
| 6,712,121 B2 * | 3/2004 | Clark et al. | 164/161 |
| 6,756,076 B2 * | 6/2004 | Brier | 427/379 |
| 6,756,127 B2 * | 6/2004 | Kuroda et al. | 428/447 |
| 6,759,127 B1 * | 7/2004 | Smith et al. | 428/395 |
| 7,178,323 B2 | 2/2007 | Kolmes et al. | |
| 7,214,425 B2 | 5/2007 | Kolmes et al. | |
| 2001/0055651 A1 | 12/2001 | Mao et al. | |
| 2003/0064645 A1 | 4/2003 | Worley et al. | |
| 2004/0261195 A1 | 12/2004 | Ghosh et al. | |
| 2007/0094761 A1 | 5/2007 | Kolmes et al. | |
| 2007/0099528 A1 | 5/2007 | Kolmes et al. | |
| 2007/0137164 A1 | 6/2007 | Kolmes et al. | |
| 2007/0144135 A1 | 6/2007 | Kolmes et al. | |
| 2007/0271965 A1 | 11/2007 | Kolmes et al. | |

FOREIGN PATENT DOCUMENTS

| | | |
|---|---|---|
| CN | 1203293 | 12/1998 |
| EP | 0 908 553 A2 | 4/1999 |
| JP | 59-71480 | 4/1984 |
| JP | 7-268780 | 10/1995 |
| JP | 2002-509994 | 4/2002 |
| WO | WO 99/35315 | 7/1999 |
| WO | WO 99/50062 | 10/1999 |
| WO | WO 02/064668 A1 | 8/2002 |
| WO | WO 03/032726 A1 | 4/2003 |

OTHER PUBLICATIONS

Office Action issued Jul. 23, 2010, in European Patent Application No. 05 723 657.2, filed Feb. 25, 2005.

* cited by examiner

*Primary Examiner* — Robert A Wax
*Assistant Examiner* — Melissa S Mercier
(74) *Attorney, Agent, or Firm* — Oblon, Spivak, McClelland, Maier & Neustadt, L.L.P.

(57) ABSTRACT

A process for providing antimicrobial properties to a composite item, such as a composite yarn, composite fabric or composite article, is provided involving the steps of immersing the composite item in a aqueous bath containing an organic antimicrobial agent, separating the immersed composite item from the bath and drying the separated composite item, and the antimicrobial composite items provided therefrom.

15 Claims, No Drawings

US 7,939,686 B2

METHOD FOR PROVIDING ANTIMICROBIAL COMPOSITE YARNS, COMPOSITE FABRICS AND ARTICLES MADE THEREFROM

U.S. application Ser. No. 10/785,060

BACKGROUND OF THE INVENTION

1. Field of Invention

The present invention relates to a method for providing antimicrobial properties to composite yarns, composite fabrics or composite articles in a simple post-production process, and the antimicrobial composite yarns, fabrics or articles provided therefrom.

2. Discussion of the Background

There are currently many types of antimicrobial fiber based products on the market. There are two basic methods for providing antimicrobial properties: 1) a poisoning method and 2) a contact kill method. In the poisoning method, the products are conventionally prepared by the incorporation of silver ions (either in the form of salts or as silver ion containing ceramics) onto the surface of the product or, in the case of polymeric based products, into the interior of the polymer by addition to the polymer melt. The silver ions then infiltrate the microbes and prevent reproduction. The downside to this method, of course, is that it takes time and the silver ions are naturally depleted, as they must come off of the product and infiltrate the microbe in order to work.

In the contact kill method, an antimicrobial agent is applied to the external surface of individual fibers or yarns or dissolved in a polymer melt prior to formation of the fibers or yarns, which upon contacting the microbe causes its death. U.S. Pat. No. 5,567,372 discloses the use of a siloxane quaternary ammonium salt based antimicrobial agent by incorporation into the polymer melt prior to fiber formation. U.S. Patent Application Publication 2003/0064645 discloses the preparation of biocidal polyester fabrics, fibers and other materials using a process that requires treatment of the polyester to provide active functional groups to which a heterocyclic N-halamine is then covalently bonded to render the polyester antimicrobial. U.S. Pat. No. 6,596,657 discloses a method for providing antimicrobial properties particularly for polypropylene and nylon containing fabrics by initial phosphonylation of the polymer fiber surface, or for non-modified surfaces by using a non-volatile salt of an antimicrobial agent such as triclosan, or by complexing iodine with a polymer containing grafted amide-bearing chains. However, all of these methods have in common the need to create the antimicrobial properties at the polymer level, either during preparation of the polymer itself, or by surface modification of the polymer fibers by chemical reaction.

In the area of composite fibers, some effort has been expended to create antimicrobial products. Since composite fibers are often used to prepare cut-proof gloves and other articles often used in meat packaging and similar industries where there are potentially high levels of bacteria, an antimicrobial composite fiber product would be very useful. U.S. Pat. No. 6,351,932; WO 99/35315; and U.S. Pat. No. 6,266,951 each disclose antimicrobial properties in a composite fiber. However, in each case, these properties are generated by forming the composite fiber from a component that has been provided with antimicrobial properties prior to incorporation into the composite fiber. Thus, in each of these cases, it is necessary for the fiber manufacturer to either purchase the antimicrobial component for use in preparation of the composite fiber, or to prepare the individual antimicrobial component themselves, prior to incorporation into the composite fiber.

In each of U.S. Pat. Nos. 6,384,254 and 5,707,736 are described methods for treating fabrics with an antimicrobial composition. U.S. Pat. No. 6,384,254 discloses the use of a quaternary ammonium salt containing polysiloxane solution to treat a fabric by dipping, spraying or roll coating to give a controlled coating weight of the antimicrobial on the fabric, followed by drying with blowing hot air or in a heating furnace at 100-150 C. In U.S. Pat. No. 5,707,736 is described a continuous process for treating a fabric by immersion of the fabric in a tub of diluted antimicrobial agent, followed by pressing to partially dry, followed by drying in a hot air blowing chamber or hot drum chamber at a temperature of up to 120 C., followed by winding of the fabric, which is then used as a dressing or support. However, again each of these methods is used by the fabric manufacturer using equipment and conditions not readily available to the ordinary consumer and typically not involving articles of finished goods containing multiple types of fibers, yarns or other materials.

Accordingly, there is a need for a method for providing antimicrobial properties to yarns, fabrics and finished articles containing two or more different types of fibers or yarns (i.e. composite yarns, composite fabrics or composite articles, respectively), which can be readily performed by the consumer, or by the manufacturer after production of the finished product.

SUMMARY OF THE INVENTION

Accordingly, one object of the present invention is to provide a process for providing antimicrobial properties to a composite yarn.

A further object of the present invention is to provide a process for providing antimicrobial properties to a composite fabric.

Another object of the present invention is to provide a process for providing antimicrobial properties to an composite article comprising a composite yarn or fabric.

Another object of the present invention is to provide a composite item selected from These and other objects of the present invention have been satisfied by the discovery of a method for providing antimicrobial properties to a composite item, comprising:

immersing a composite item in an aqueous bath comprising an organic antimicrobial agent;

separating the immersed composite item from the bath; and drying the separated composite item, wherein the composite item is a member selected from the group consisting of composite yarns, composite fabrics and composite articles, and the antimicrobial composite items prepared therefrom.

DETAILED DESCRIPTION OF THE INVENTION

The term "fiber" as used herein refers to a fundamental component used in the assembly of yarns and fabrics. Generally, a fiber is a component which has a length dimension which is much greater than its diameter or width. This term includes ribbon, strip, staple, and other forms of chopped, cut or discontinuous fiber and the like having a regular or irregular cross section. "Fiber" also includes a plurality of any one of the above or a combination of the above.

As used herein, the term "high performance fiber" means that class of synthetic or natural non-glass fibers having high values of tenacity greater than 10 g/denier, such that they lend themselves for applications where high abrasion and/or cut resistance is important. Typically, high performance fibers have a very high degree of molecular orientation and crystallinity in the final fiber structure.

The term "filament" as used herein refers to a fiber of indefinite or extreme length such as found naturally in silk. This term also refers to manufactured fibers produced by, among other things, extrusion processes. Individual filaments making up a fiber may have any one of a variety of cross sections to include round, serrated or crenular, bean-shaped or others.

The term "yarn" as used herein refers to a continuous strand of textile fibers, filaments or material in a form suitable for knitting, weaving, or otherwise intertwining to form a textile fabric. Yarn can occur in a variety of forms to include a spun yarn consisting of staple fibers usually bound together by twist; a multi filament yarn consisting of many continuous filaments or strands; or a mono filament yarn which consist of a single strand.

The term "air interlacing" as used herein refers to subjecting multiple strands of yarn to an air jet to combine the strands and thus form a single, intermittently commingled strand. This treatment is sometimes referred to as "air tacking." This term is not used to refer to the process of "intermingling" or "entangling" which is understood in the art to refer to a method of air compacting a multifilament yarn to facilitate its further processing, particularly in weaving processes. A yarn strand that has been intermingled typically is not combined with another yarn. Rather, the individual multifilament strands are entangled with each other within the confines of the single strand. This air compacting is used as a substitute for yarn sizing and as a means to provide improved pick resistance. This term also does not refer to well known air texturizing performed to increase the bulk of single yarn or multiple yarn strands. Methods of air interlacing in composite yarns and suitable apparatus therefore are described in U.S. Pat. Nos. 6,349,531; 6,341,483; and 6,212,914, the contents of which are hereby incorporated by reference.

The term "composite yarn" refers to a yarn prepared from two or more yarns, which can be the same or different. Composite yarn can occur in a variety of forms wherein the two or more yarns are in differing orientations relative to one another. The two or more yarns can, for example, be parallel, wrapped one around the other(s), twisted together, or combinations of any or all of these, as well as other orientations, depending on the properties of the composite yarn desired. Examples of such composite yarns are provided in U.S. Pat. Nos. 4,777,789; 5,177,948; 5,628,172; 5,845,476; 6,351,932; 6,363,703 and 6,367,290, the contents of which are hereby incorporated by reference.

The term "composite fabric" is used herein to indicate a fabric prepared from two or more different types of yarn or composite yarn. The fabric construction can be any type, including but not limited to, woven, knitted, non-woven, etc. The two or more different types of yarn or composite yarn include, but are not limited to, those made from natural fibers, synthetic fibers and combinations thereof.

The term "composite article" is used herein to indicate a final article that comprises at least two different types of materials. The composite article can be prepared from a composite fabric, or can be prepared from a conventional fabric containing only one type of yarn, but is put together using a yarn or sewing thread made of a different material. Alternatively, the conventional fabric can be sewn together using a composite yarn as the sewing thread. Composite articles can be any form, including but not limited to, gloves, aprons, socks, filters, shirts, pants, undergarments, one-piece jumpsuits, etc. All of these types of articles, as well as other permutations that are readily evident to those of skill in the art, are included in the present invention definition of "composite article".

The present invention relates to a method for providing antimicrobial properties to a composite yarn, composite fabric or composite article. The method comprises immersion of the composite yarn, fabric or article in an aqueous solution/emulsion/dispersion of an organic antimicrobial agent, draining excess water from the yarn, fabric or article, followed by drying the composite yarn, fabric or article using a heater, preferably at a temperature of from 50-100° C. Preferably the heater has forced blowing hot air at the desired temperature to assist in carrying off the moisture being liberated from the treated product. Alternatively, the heater can operate under reduced pressure if desired, to further lower the temperature and remove moisture being liberated.

As antimicrobial agent for use in the present invention, one can use any conventional organic (i.e. non-silver ion containing) antimicrobial agent. Preferably, the antimicrobial agent is a silicone based quaternary ammonium salt, more preferably a copolymer (which may or may not include partially or fully hydrolyzed forms) of a long chain ($C_{12}$-$C_{20}$) alkyldimethylaminotrihydroxysilylpropyl ammonium halide and a chloroalkyltrihydroxysilane. Particularly preferred for use as the antimicrobial agent is a copolymer (which may or may not include partially or fully hydrolyzed forms) of octadecylaminodimethyltrihydroxysilylpropyl ammonium chloride and chloropropyltrihydroxysilane. Suitable such antimicrobials include, but are not limited to, the Bioshield line of antimicrobial agents available from NovaBioGenetics, Inc., antimicrobials such as those used to prepare the Biokryl products from Acordis, or the antimicrobial agents from Aegis Environments such as AEM 5700 Antimicrobial, AEM 5772 Antimicrobial and AEGIS Antimicrobial. The antimicrobial agent is used as an aqueous solution/emulsion/dispersion (depending on the solubility of the agent itself). When necessary for the creation of an emulsion or dispersion, any conventional emulsifier or dispersant can be used, so long as it can be readily washed away from the surface of the yarn, fabric or article using water and a detergent. Preferably the antimicrobial agent is present in the antimicrobial agent bath in an amount of from 0.1-2% by weight, more preferably from 0.1-1% by weight, most preferably from 0.3-0.7% by weight. If the antimicrobial agent is received from the supplier at a higher percentage that desired, the agent can be diluted as needed to provide the desired strength of solution/emulsion/dispersion.

For providing antimicrobial properties to a composite yarn, the present process can be used with the composite yarn at any stage after assembly of the yarn. If used in a continuous type process (within the context of the present invention a continuous type process includes both truly continuous processes and semi-continuous processes in which there are periodic stops for product type changes, other line modifications or for any other reason), the application of the antimicrobial liquid can be performed after assembly but prior to take up on a yarn package or bobbin. The application in such a continuous process can be done by immersion through a bath, followed by drying using an in-line dryer. Drying can alternatively be performed in such a continuous process by use of a heated drying roll around which the composite yarn is wrapped. Drying time can be adjusted based upon the size of the drying roll and the number of wraps of yarn around the roll. In a batch type process, the composite yarn is assembled, taken up on a bobbin, then the entire composite yarn package (yarn wound around the bobbin) is immersed in the antimicrobial agent bath. After immersion for a period of time sufficient to provide complete penetration of the antimicrobial agent liquid throughout the bobbin (preferably from 5-60 seconds), the package is removed from the bath, excess water drained, and the package placed in a heater at the drying temperature.

For providing antimicrobial properties to a composite fabric, the present process can likewise be used at any stage after formation of the fabric, either in a continuous type process or in a batch type process. As in the composite yarn case, the continuous type process for a composite fabric can be performed by applying the antimicrobial liquid after formation of the fabric (i.e. after weaving, knitting or forming the non-woven web), but prior to take up of the fabric on a roll. The application of the antimicrobial agent can be done by immersion through a bath, followed by drying the fabric using an in-line dryer. As in the composite yarn case, the composite fabric can also be rendered antimicrobial in a batch type process by immersion of an entire roll of the fabric, draining of the excess water, and placing the roll in a heater at the drying temperature.

In a preferred embodiment of the present process, the process is used on a composite article to provide antimicrobial properties. This embodiment is most preferred in that it can be readily accomplished by the consumer using a conventional household washer and dryer. In this embodiment, the antimicrobial agent is added to the washer before or during the wash cycle. After washing, the treated composite article is placed in the household dryer and dried at a temperature of approximately 70-90° C. The resulting composite article has antimicrobial properties which will last for at least 20 wash cycles, more preferably for at least 40 wash cycles, most preferably up to 50 wash cycles without the need for replenishment.

The present process can be used on any articles, including those made from synthetic fibers or yarns, those made from natural fibers or yarns, leather products, and articles that contain any or all of these. Suitable articles include any article of clothing or protective wear, such as shoes, socks, gloves, as well as filtering media.

A further preferred embodiment of the present invention provides for recycling of the spent liquid containing the antimicrobial agent, for use on other composite yarns, composite fabrics or composite articles. Conventionally, when manufacturers prepare antimicrobial products by immersion of a product (as opposed to incorporation into the internal structure of the product components themselves), the spent antimicrobial agent containing liquid is disposed of after a single use. Applicants have found that by recycling the spent antimicrobial agent containing liquid, multiple repetitions of the process can be performed without the need to replenish the level of antimicrobial agent. Even then, all that is needed is to add enough antimicrobial agent to the liquid to bring the amount of agent up to the desired level.

One major advantage in this method is the cost savings that result from the recycling of the antibacterial agent solution. This makes the treatment less expensive than most products used in the field today. Another advantage is that the treated products are washable with other basic wash items, towels and underwear etc. Normal bleach and detergents are also no problem and do not detract from the antibacterial properties of the product. Quite the contrary, the use of bleach can actually be advantageous as mentioned below. Once the present process has been performed on a composite yarn, fabric or article, the antimicrobial properties are robust and survive through multiple wash/dry cycles (as noted above). These properties can also be replenished or reactivated by washing or treating the used yarn, fabric or article in a hypochlorite containing bleach solution, such as the conventional sodium hypochlorite.

While the process of the present invention can be performed at any bath pH, it is preferred that the pH be slightly basic, more preferably $\geq 8$, most preferably $\geq 9$. At these higher pH's the resulting treated product has greater durability of the antimicrobial properties.

The present process provides the ability to readily treat yarns, fabrics and articles made from more than one type of material and impart antimicrobial properties to the entire product, regardless of its composition. Further, the present process does not require the use of pressurized equipment, as is often conventionally done when attempting to infiltrate an entire bobbin of yarn or roll of fabric. The present process is readily performed on finished articles by the consumer, or on assembled composite yarns or composite fabrics by the yarn or fabric manufacturer, with relative ease and with little added cost. Even better is the ability to recycle the antimicrobial agent bath used in the process for added cost savings. Further, by using organic antimicrobial agents (instead of silver ion based antimicrobials) and the lower drying temperatures of the present process, the resulting antimicrobial products do not experience the discoloration that occurs with silver based antimicrobials, or that can occur due to heat degradation of other antimicrobial agents.

Obviously, additional modifications and variations of the present invention are possible in light of the above teachings. It is therefore to be understood that within the scope of the appended claims, the invention may be practiced otherwise than as specifically described herein.

The invention claimed is:

1. A method for providing antimicrobial properties to a composite item, comprising:
    immersing a composite item in an aqueous bath comprising an organic antimicrobial agent, wherein said organic antimicrobial agent is silicone based quaternary ammonium salt that is a copolymer of a long chain ($C_{12}$-$C_{20}$) alkyldimethylaminotrihydroxysilylpropyl ammonium halide and a chloroalkyltrihydroxysilane;
    separating the immersed composite item from the bath; and
    drying the separated composite item at a temperature of from 50-90° C., wherein the composite item is a member selected from the group consisting of composite yarns, composite fabrics and composite articles;
    wherein the resulting composite item retains antimicrobial properties for at least 40 wash cycles;
    wherein the antimicrobial properties can be regenerated after one or more uses by contacting the treated item with a hypochlorite solution.

2. The method of claim 1, further comprising the step of reusing the bath in a further immersing step on a different composite item.

3. The method of claim 1, wherein said composite item is a composite yarn.

4. The method of claim 1, wherein said composite item is a composite fabric.

5. The method of claim 1, wherein said composite item is a composite article.

6. The method of claim 5, wherein said composite article is a member selected from the group consisting of gloves, aprons, socks, filters, shirts, pants, undergarments, and one-piece jumpsuits.

7. The method of claim 3, wherein said process is a continuous process.

8. The method of claim 3, wherein said process is a batch process and said composite yarn is in a form of composite yarn wound on a bobbin.

9. The method of claim 4, wherein said process is a continuous process.

10. The method of claim 4, wherein said process is a batch process and said composite fabric is in a form of composite fabric wound on a roll.

11. The method of claim 1, wherein said organic antimicrobial agent is present in said bath in an amount of from 0.1-2% by weight of the total bath.

12. The method of claim 1, wherein said silicone based quaternary ammonium salt is a copolymer of octadecylaminodimethyltrihydroxysilylpropyl ammonium chloride and chloropropyltrihydroxysilane.

13. The method of claim 5, wherein said immersing step is performed in a household clothes washer and said drying step is performed in a household clothes dryer.

14. The method of claim 1, wherein said drying step is performed at a temperature of from 70-90° C.

15. A composite item selected from the group consisting of composite yarns, composite fabrics and composite articles, having antimicrobial properties and prepared by the method of claim 1.

\* \* \* \* \*